United States Patent [19]

Berris

[11] Patent Number: 5,292,969
[45] Date of Patent: Mar. 8, 1994

[54] PHENOLIC ANTIOXIDANT AND PROCESS
[75] Inventor: Bruce C. Berris, Baton Rouge, La.
[73] Assignee: Ethyl Corporation, Richmond, Va.
[21] Appl. No.: 41,097
[22] Filed: Apr. 1, 1993
[51] Int. Cl.⁵ .............................................. C07C 39/12
[52] U.S. Cl. .................................... 568/720; 568/719
[58] Field of Search ................ 568/714, 770, 719, 720

[56] References Cited

U.S. PATENT DOCUMENTS

| | | | |
|---|---|---|---|
| 4,259,534 | 3/1981 | Gurvich et al. | 568/720 |
| 4,870,214 | 9/1989 | Mina et al. | 568/720 |
| 4,898,994 | 2/1990 | Livingston et al. | 568/720 |
| 4,992,597 | 2/1991 | Mina et al. | 568/719 |
| 4,994,628 | 2/1991 | Goddard et al. | 568/720 |

FOREIGN PATENT DOCUMENTS

| | | | |
|---|---|---|---|
| 2745879 | 4/1978 | Fed. Rep. of Germany | 568/720 |
| 56-92237 | 7/1981 | Japan | 568/720 |
| 61-30544 | 2/1986 | Japan | 568/720 |

Primary Examiner—James H. Reamer
Attorney, Agent, or Firm—Patricia J. Hogan

[57] ABSTRACT

A 1,3,5-trimethyl-2,4,6-tris(3,5-dialkyl-4-hydroxybenzyl)benzene is prepared in high yield by reacting a 2,6-dialkyl-4-methoxymethylphenol with mesitylene in a hydrocarbon solvent and in the presence of at least about 10 mol %, based on the amount of mesitylene, of a hydrocarbon-soluble acid (e.g., an alkylbenzenesulfonic acid having 12-18 carbons in the alkyl group, a carboxylic acid, or a dialkylsulfosuccinate) as a catalyst or co-catalyst while distilling methanol by-product out of the reaction mixture as it is formed. The process may be conducted so as to provide a substantially pure product or a product, such as 1,3,5-trimethyl-2,4,6-tris(3,5-di-t-butyl-4-hydroxybenzyl)benzene, having fairly high purity (e.g., about 98-98%) and a melting point much lower than would be expected of a product having such high purity.

17 Claims, No Drawings

PHENOLIC ANTIOXIDANT AND PROCESS

Field of Invention

This invention relates to 1,3,5-trimethyl-2,4,6-tris(3,5-dialkyl-4-hydroxybenzyl)benzenes and more particularly to a process for preparing them and to novel products obtainable by the process.

BACKGROUND

It is known that 1,3,5-trimethyl-2,4,6-tris(3,5-dialkyl-4-hydroxybenzyl)benzenes can be prepared by reacting mesitylene with the appropriate 2,6-dialkyl-4-methoxymethylphenol in the presence of an acidic catalyst, usually sulfuric acid. It is also known that the use of sulfuric acid in an amount sufficient to provide the desired product in good yields has presented a severe spent sulfuric acid disposal problem in commercial operations.

As taught in U.S. Pat. Nos. 4,992,597 (Mina et al.) and 4,994,628 (Goddard et al.), this disposal problem can be minimized by conducting the mesitylene/2,6-dialkyl-4-methoxymethylphenol reaction under temperature and pressure conditions such that methanol by-product formed by the reaction distills out of the reaction mixture as it is formed. The co-distillation technique permits the desired product to be provided in high yield with the use of considerably smaller amounts of sulfuric or sulfonic acid catalyst than were previously thought necessary to provide a 1,3,5-trimethyl-2,4,6-tris(3,5-dialkyl-4-hydroxybenzyl)benzene containing commercially-unacceptable amounts of by-products.

Although Mina et al. and Goddard et al. teach that their reactions may be conducted in hydrocarbon solvents instead of their preferred halohydrocarbon solvents, it has not been found possible to obtain good product yields when a hydrocarbon solvent is employed. This is particularly unfortunate because of the present desirability of avoiding the use of halohydrocarbon solvents—especially those which are already highly regulated and believed to be potentially damaging to the ozone layer.

SUMMARY OF INVENTION

It has now been discovered that a 1,3,5-trimethyl-2,4,6-tris(3,5-dialkyl-4-hydroxybenzyl)benzene can be prepared in high yield when a 2,6-dialkyl-4-methoxymethylphenol is reacted with mesitylene in a hydrocarbon solvent and in the presence of at least about 10 mol %, based on the amount of mesitylene, of a hydrocarbonsoluble acid as a catalyst or co-catalyst while distilling methanol by-product out of the reaction mixture as it is formed. Moreover, this process may be conducted so as to provide a substantially pure product or alternatively a novel product which, although having a purity of about 95-98%, has a melting point considerably lower than the melting point of the pure product.

DETAILED DESCRIPTION

The 2,6-dialkyl-4-methoxymethylphenol which is reacted with mesitylene in the practice of the invention may be any one or more of the 2,6-dialkyl-4-methoxymethylphenols of Mina et al. and Goddard et al., the teachings of which are incorporated herein by reference. Thus, as in Mina et al. and Goddard et al., the "alkyl" groups in the 2- and 6-positions may be alkyl, cycloalkyl, or aralkyl groups and may be the same or different; and the phenols include, e.g., the 2,6-dimethyl-, 2,6-diisopropyl-, 2,6-diisobutyl-, 2,6-di-sec-butyl-, 2,6-di-t-butyl-, 2,6-dicyclopentyl-, 2,6-dicyclohexyl-, 2,6-dibenzyl-, 2,6-di($\alpha$-methylbenzyl)-, 2-methyl-6-t-butyl-, 2-methyl-6-t-octyl-, 2-methyl-6-cyclopentyl-, 2-methyl-6-benzyl-, 2-methyl-6-($\alpha$-methylbenzyl)-, 2-isopropyl-6-($\alpha,\alpha$-dimethylbenzyl)-, and 2-t-butyl-6-cyclooctyl-4-methoxymethylphenols. The preferred phenol is 2,6-di-t-butyl-4-methoxymethylphenol.

As is customary in 1,3,5-trimethyl-2,4,6-tris(3,5-dialkyl-4-hydroxybenzyl)benzene syntheses, the 2,6-dialkyl-4-methoxymethylphenol is employed in a stoichiometric sufficiency or excess, usually an amount such as to provide about 3-5, preferably about 3.3-4.0 mols of the phenol per mol of mesitylene.

The hydrocarbon used as a solvent may be any suitable aliphatic or cycloaliphatic hydrocarbon, e.g., cyclohexane, hexane, heptane, octane, isooctane, or nonane. However, it is preferably heptane. It may be employed in any amount appropriate to its purpose of serving as the reaction medium (e.g., about 150-1000 parts/100 parts by weight of the reactants); and some of that amount may be reserved from the initial charge to the reaction vessel, if desired, and added together with the phenol.

As already mentioned, the process of the invention utilizes at least 10 mol %, based on the amount of mesitylene, of a hydrocarbon-soluble acid as a catalyst or co-catalyst. This hydrocarbon-soluble acid, which may be used in the form of a salt, is an acid which is soluble in the hydrocarbon employed as a reaction solvent; and it may be selected from any such materials which are commonly used as surfactants, e.g., alkylbenzenesulfonic acids having 12-18 carbons in the alkyl chain, carboxylic acids such as stearic acid, sodium dioctylsulfosuccinate, and other dialkylsulfosuccinates.

It is important for the reaction mixture of contain at least the aforementioned minimum amount of the hydrocarbon-soluble acid in order to avoid the formation of such large amounts of by-products, mainly methylenebis(2,6-dialkylphenols), that the 1,3,5-trimethyl-2,4,6-tris(3,5-dialkyl-4-hydroxybenzyl)benzenes—if formed at all—would be formed in considerably decreased yields. From the aspect of accomplishing high yields of the desired products, there does not appear to be any maximum to the amount of hydrocarbon-soluble acid that may be used. However, as a practical matter, it is ordinarily unnecessary to employ an amount greater than about 25 mol %, based on the amount of mesitylene; and the concentrations most commonly used are in the range of about 15-20 mol %, based on the amount of mesitylene.

The hydrocarbon-soluble acid is preferably used as a co-catalyst with one of the catalysts more conventionally used in this type of reaction (i.e., sulfuric acid or a sulfonic acid of Mina et al.) in order to increase the yield of the desired product. As in Goddard et al. a sulfuric acid utilized in the reaction is a concentrated sulfuric acid, i.e., a sulfuric acid having a concentration of 75-100%, most preferably 80-98% by weight. Sulfonic acids utilizable as an optional component of the catalyst are sulfonic acids which, unlike the essential component of the catalyst, are usually insoluble in hydrocarbons and which, when they include an alkylbenzene moiety, lack the long alkyl chains of the alkylbenzenesulfonic acids mentioned above. Exemplary of such sulfonic acids are aliphatic sulfonic acids, such as methanesulfonic acid, ethanesulfonic acid, propanesulfonic acid, trichloromethanesulfonic acid, and trifluoromethanesulfonic acid; and aromatic sulfonic acids, such as benzenesulfonic acid, o-, m-, and p-toluenesulfonic acids, chlorobenzenesulfonic acid, and chlorotoluenesulfonic acid.

When one of these conventional catalysts is employed, it may be utilized in the large amount once customarily used or in the somewhat smaller amounts taught by Mina et al. and Goddard et al. However, it is usually preferred to use still smaller amounts of a sulfuric or sulfonic acid catalyst in the present reaction, e.g., about 0.1–0.5 mol per mol of mesitylene.

Like the processes of Mina et al. and Goddard et al., the present process is conducted by slowly adding the 2,6-dialkyl-4-methoxymethylphenol to a reaction vessel containing the mesitylene, the catalyst or catalysts, and at least a portion of the solvent under conditions such as to permit distillation of methanol from the reaction mixture as it is formed. The temperature employed for the reaction is usually a temperature in the range of about 20°–150° C., and the pressure should be such as to permit distillation of the methanol from the reaction mixture without the co-distillation of excessive amounts of hydrocarbon solvent. As in Mina et al. and Goddard et al., it is usually necessary to maintain a partial vacuum during the reaction in order to achieve the appropriate temperature and pressure conditions to permit the methanol distillation.

The distillate removed from the reaction mixture could be discarded if it were desired to replace its hydrocarbon content with fresh hydrocarbon solvent added together with the 2,6-dialkyl-4-methoxymethylphenol. However, it is preferable to separate the hydrocarbon and methanol in the distillate (e.g., by passing the distillate through an adsorbent having an affinity for methanol, such as 4A molecular sieves, or separating the two phases using a Dean-Stark trap) and recycle the distillate from which the methanol has been removed. Most preferably, this is accomplished by conducting the reaction in equipment designed to permit the refluxing hydrocarbon to contact and dissolve the 2,6-dialkyl-4-methoxymethylphenol feed as the hydrocarbon is recycled, thus simultaneously accomplishing dissolution of the phenol, feeding of the phenol, and recycling of solvent.

Because of the use of the hydrocarbon solvent, the product of the reaction is obtainable as a slurried solid which can be easily separated either by filtering it directly from the reaction mixture and washing it or by crystallizing it after dilution from water.

The invention is advantageous, not only in its providing a high yield process for preparing a 1,3,5-trimethyl-2,4,6-tris(3,5-dialkyl-4-hydroxybenzyl)benzene in a hydrocarbon solvent and in the presence of little or no sulfuric or sulfonic acid catalyst, but in its permitting the formation of substantially pure 1,3,5-trimethyl-2,4,6-tris(3,5-dialkyl-4-hydroxybenzyl)benzenes or 1,3,5-trimethyl-2,4,6-tris(3,5-dialkyl-4-hydroxybenzyl)benzenes that have a purity of about 95–98%, are free of methylenebis(2,6-dialkylphenol) by-products, and contain small amounts of 1,3,5-trimethyl-2,4-bis(3,5-dialkyl-4-hydroxybenzyl)benzenes which can effect a much greater reduction in the melting points of the products than would be expected from their concentration. For example, 1,3,5-trimethyl-2,4,6-tris(3,5-di-t-butyl-4-hydroxybenzyl)benzene can be prepared by the process of the invention so as to have a purity of about 95–98%, contain 1,3,5-trimethyl-2,4-bis(3,5-di-t-butyl-4-hydroxybenzyl)benzene as its only detectable impurity, and have a melting point in the range of about 195°–200° C., whereas pure 1,3,5-trimethyl-2,4,6-tris(3,5-di-t-butyl-4-hydroxybenzyl)benzene has a melting point of 244° C.

The ability of the invention to provide low-melting, high-purity products is a particularly desirable feature when the product is to be used as an antioxidant for a polymer which could be compounded more easily with a lower melting antioxidant. Moreover, the lower melting point of the product could also allow it to react faster to stop chain scission in polypropylene or other normally oxidizable polymer being stabilized and thus improve the melt index of the stabilized material.

The following examples are given to illustrate the invention and are not intended as a limitation thereof.

EXAMPLE 1

Charge 547 mg (4.55 mmols) of mesitylene, 294 mg (0.858 mmols) of $C_{12-14}$ alkylbenzenesulfonic acid, 192 mg (1.998 mmols) of methanesulfonic acid, and 25 mL of hexanes to a suitable reaction vessel fitted with a Dean-Stark trap having a bottom return and charged with 12 g of 4A molecular sieves, 5.77 g (23.0 mmols) of 2,6-di-t-butyl-4-methoxymethylphenol, and sufficient hexanes to fill the trap. Heat the reaction mixture to reflux at a bath temperature of 78° C. under a partial vacuum maintained to give a constant reflux. While slowly adding the phenol to the reaction mixture by its gradual dissolution in refluxing hexanes until it is completely dissolved, remove the methanol by-product from the reaction mixture by azeotropic distillation and then remove it from the distillate by absorption into the molecular sieves. Then cool the resultant suspension of white solid in a deep blue reaction mixture, and add aqueous sodium carbonate to give a light orange solution and white solid. Suction-filter and vacuum-dry the product to provide 2.64 g of 1,3,5-trimethyl-2,4,6-tris(3,5-di-t-butyl-4-hydroxybenzyl)benzene—a 74% yield based on mesitylene.

COMPARATIVE EXAMPLE A

Repeat Example 1 except for employing no $C_{12-14}$ alkylbenzenesulfonic acid. The product is primarily methylenebis(2,6-di-t-butylphenol) and partially benzylated mesitylenes.

EXAMPLE 2

Charge 0.567 g (1.28 mmols) of sodium dioctylsulfosuccinate, 18 g of heptane, 0.9094 g (7.57 mmols) of mesitylene, and 0.143 g (1.385 mmols) of concentrated sulfuric acid to a flask which is attached to a glass tube containing a coarse fritted-glass filter and charged with 7.46 g (29.79 mmols) of 2,6-di-t-butyl-4-methoxymethylphenol. Heat the mixture to reflux at a bath temperature of 50° C. while maintaining a vacuum to 51 mm Hg. While slowly and continuously adding the phenol by its gradual dissolution in refluxing heptane until it is completely added, remove the methanol by-product from the reaction mixture by co-distillation and subsequently separate it from the condensate in a Dean-Stark trap connected to the top of the glass tube. Admit nitrogen to the apparatus, and then add 4 mL of water to the reaction mixture. Analysis of a sample of the orange slurry thus obtained shows it to consist mainly of 1,3,5-trimethyl-2,4,6-tris(3,5-butyl-4-hydroxybenzyl)benzene, 1,3,5-trimethyl-2,4-bis(3,5-di-t-butyl-4-hydroxybenzyl)- benzene, and 4,4'-methylenebis(2,6-di-t-butylphenol) in a mol ratio of 15/1/4.

Transfer the contents of the flask to another flask, add 15 mL of heptane, and heat the mixture to reflux with stirring until the solid is dissolved. Allow the phases to separate while still hot, remove the lower phase, and then wash the organic phase with hot water (2×14 mL) and allow it to cool slowly overnight. Filtration, washing, and drying of the white precipitate thus obtained yields 4.169 g of a 1,3,5-trimethyl-2,4,6-tris(3,5-di-t-butyl-4-hydroxybenzyl)benzene product having a melting point of 198°–199° C. and a purity of 98% by GC analysis. The yield is 71%, based on mesitylene.

EXAMPLE 3

Essentially repeat the reaction of Example 2 except for using 0.573 g (1.29 mmols) of sodium dioctylsulfosuccinate, 14 g of heptane 0.9007 g (7.49 mmols) of mesitylene, 135 mg (1.31 mmols) of the concentrated sulfuric acid, and 7.45 g (29.75 mmols) of the phenol. After completing addition of the phenol, add 2.0 mL of a 30% aqueous solution of sodium carbonate, filter the product from the orange slurry thus obtained, wash the product with heptane and water, and vacuum-dry to provide 5.49 g of a 1,3,5-trimethyl-2,4,6-tris(3,5-di-t-butyl-4-hydroxybenzyl)benzene product having a melting point of 195°–197° C. and a purity of 95% by GC analysis. The remaining 5% of the product is 1,3,5-trimethyl-2,4-bis(3,5-di-t-butyl-4-hydroxybenzyl)benzene. After correcting for the purity, the calculated yield of the desired product is 90%, based on mesitylene.

EXAMPLE 4

Essentially repeat the reaction of Example 2 except for using 0.622 g (1.399 mmols) of sodium dioctylsulfosuccinate, 20 g of n-heptane, 0.139 g (1.35 mmols) of the sulfuric acid, 1.0242 g (8.52 mmols) of mesitylene, 7.56 g (30.2 mmols) of the phenol, and pressure/temperature conditions of 60 mm Hg and 35° C. After completing addition of the phenol, add 5 mL of water, then add 15 mL of heptane to the orange slurry thus obtained, reflux the resultant mixture to dissolve the slurry, and remove the lower layer containing an aqueous solution of dioctylsulfosuccinate. Wash the organic phase with water (2×20 mL) and allow it to cool slowly to 5° C. Filtration, washing with heptane, and drying give 4.98 g of a white 1,3,5-trimethyl-2,4,6-tris(3,5-di-t-butyl-4-hydroxybenzyl)benzene product having a melting point of 242°–244° C.—a 75% yield based on mesitylene.

COMPARATIVE EXAMPLE B

Repeat Example 2 except for using no sodium dioctylsulfosuccinate. The product is primarily methylenebis(2,6-di-t-butylphenol) and partially benzylated mesitylenes.

COMPARATIVE EXAMPLE C

Repeat Example 2 except for using 0.262 g (0.59 mmol) of sodium dioctylsulfosuccinate, 18 g of heptane, 0.079 g (0.765 mmol) of the sulfuric acid, 0.903 g (7.51 mmols) of mesitylene, and 6.59 g (26.32 mmols) of the phenol—providing only 0.079 mol of the hydrocarbon-soluble catalyst per mol of mesitylene instead of the 0.169/1 mol ratio provided in Example 2. The orange slurry contains the 1,3,5-trimethyl-2,4,6-tri(3,5-di-t-butyl-4-hydroxybenzyl)benzene 1,3,5-trimethyl-2,4-bis(3,5-di-t-butyl-4-hydroxybenzyl)benzene, and 4,4'-methylenebis(2,6-di-t-butylphenol) in a mol ratio of 5.6/1/1.7 instead of the 15/1/4 mol ratio obtained in Example 2—a significantly larger amount of byproduct and consequently a lower yield of the desired product.

What is claimed is:

1. In a process for preparing a 1,3,5-trimethyl-2,4,6-tris(3,5-dialkyl-4-hydroxybenzyl)benzene by reacting a 2,6-dialkyl-4-methoxymethylphenol with mesitylene in an aliphatic or cyclouliphatic hydrocarbon solvent while distilling methanol by-product out of the reaction mixture as it is formed, the improvement which comprises conducting the reaction in the presence of at least about 10 mol %, based on the amount of mesitylene, of a hydrocarbon-soluble acid as a catalyst.

2. The process of claim 1 wherein the hydrocarbon-soluble acid is an acidic compound selected from the group consisting of alkylbenzenesulfonic acids having 12–18 carbons in the alkyl chain, carboxylic acids, dialkylsulfosuccinates, and salts thereof.

3. The process of claim 2 wherein the hydrocarbon-soluble acid is an alkylbenzenesulfonic acid having 12–18 carbons in the alkyl chain.

4. The process of claim 2 wherein the hydrocarbon-soluble acid is a dialkylsulfosuccinate.

5. The process of claim 4 wherein the dialkylsulfosuccinate is sodium dioctylsulfosuccinate.

6. The process of claim 1 wherein the amount of the hydrocarbon-soluble acid catalyst is about 15–20 mol %, based on the amount of mesitylene.

7. The process of claim 1 conducted in the presence of sulfuric acid or a hydrocarbon-insoluble sulfonic acid as a co-catalyst.

8. The process of claim 7 wherein the co-catalyst is sulfuric acid.

9. The process of claim 7 wherein the co-catalyst is a $C_{1-2}$ alkanesulfonic acid.

10. The process of claim 7 wherein the amount of the co-catalyst is about 0.1–0.5 mol per mol of mesitylene.

11. The process of claim 1 which includes the additional step of recovering the 1,3,5-trimethyl-2,4,6-tris(3,5-dialkyl-4-hydroxybenzyl)benzene product by filtration.

12. The process of claim 1 which includes the additional step of recovering the 1,3,5-trimethyl-2,4,6-tris(3,5-dialkyl-4-hydroxybenzyl)benzene product by crystallization.

13. The process of claim 1 wherein the 2,6-dialkyl-4-methoxymethylphenol is 2,6-di-t-butyl-4-methoxymethyl phenol.

14. The process of claim 1 wherein the hydrocarbon solvent is heptane.

15. The process of claim 1 wherein 2,6-di-t-butyl-4-methoxymethylphenol is slowly added to a solution of mesitylene and sodium dioctylsulfosuccinate in heptane and allowed to react with the mesitylene while distilling methanol by-product out of the reaction mixture as it is formed.

16. The process of claim 15 which includes the additional step of recovering the 1,3,5-trimethyl-2,4,6-tris(3,5-dialkyl-4-hydroxybenzyl)benzene product by filtration.

17. The process of claim 15 which includes the additional step of recovering the 1,3,5-trimethyl-2,4,6-tris(3,5-dialkyl-4-hydroxybenzyl)benzene product by crystallization.

* * * * *